(12) United States Patent
Oka et al.

(10) Patent No.: US 7,632,688 B2
(45) Date of Patent: Dec. 15, 2009

(54) PARTICLE HAVING MAGNETIC MATERIAL INCORPORATED THEREIN, PROCESS FOR PRODUCING THE SAME, PARTICLE FOR IMMUNOASSAY AND METHOD OF IMMUNOASSAY

(75) Inventors: Takayuki Oka, Mishima-gun (JP); Izumi Omoto, Mishima-gun (JP); Haruma Kawaguchi, Yokohama (JP); Wataru Wakui, Kawasaki (JP)

(73) Assignee: Sekisui Chemical Co., Ltd., Osaka-shi (JP)

(*) Notice: Subject to any disclaimer, the term of this patent is extended or adjusted under 35 U.S.C. 154(b) by 364 days.

(21) Appl. No.: 10/553,100

(22) PCT Filed: Apr. 16, 2004

(86) PCT No.: PCT/JP2004/005515

§ 371 (c)(1),
(2), (4) Date: Oct. 13, 2005

(87) PCT Pub. No.: WO2004/092732

PCT Pub. Date: Oct. 28, 2004

(65) Prior Publication Data

US 2006/0188932 A1    Aug. 24, 2006

(30) Foreign Application Priority Data

Apr. 16, 2003 (JP) ............ 2003-111994
Oct. 21, 2003 (JP) ............ 2003-360986
Feb. 27, 2004 (JP) ............ 2004-054295

(51) Int. Cl.
*G01N 33/543* (2006.01)
*G01N 33/553* (2006.01)
*G01N 33/545* (2006.01)
*G01N 33/20* (2006.01)
*A61K 47/32* (2006.01)

(52) U.S. Cl. .................. 436/523; 436/526; 436/521; 436/73; 514/772.4

(58) Field of Classification Search ............ 436/73, 436/523, 526, 531, 532; 435/7.1; 530/402; 514/772.4; 523/223
See application file for complete search history.

(56) References Cited

U.S. PATENT DOCUMENTS 4,358,388 A    11/1982  Daniel et al.
4,568,706 A *  2/1986  Noetzel et al. ............ 521/149
4,913,812 A    4/1990  Moriguchi et al.
5,283,079 A *  2/1994  Wang et al. ............... 427/2.13
5,320,444 A    6/1994  Okada et al.
5,320,944 A    6/1994  Okada et al.
5,736,349 A *  4/1998  Sasaki et al. .............. 435/7.94
5,814,687 A    9/1998  Kasai et al.
2002/0177234 A1  11/2002  Kitawaki et al.
2004/0115433 A1  6/2004  Elaissari et al.

FOREIGN PATENT DOCUMENTS

| | | |
|---|---|---|
| JP | HEI-04-003088 | 12/1981 |
| JP | 2589618 | 7/1992 |
| JP | 6-231957 A | 4/1994 |
| JP | HEI-06-092640 | 4/1994 |
| JP | HEI-06-148189 | 5/1994 |
| JP | HEI-06-231957 | 8/1994 |
| JP | HEI-07-225233 | 8/1995 |
| JP | 9-208788 A | 8/1997 |
| JP | HEI-09-208788 | 8/1997 |
| JP | 2000-040608 | 2/2000 |
| JP | 2000-088852 | 3/2000 |
| JP | 2001-524675 | 12/2001 |
| JP | 2002-196001 | 7/2002 |
| JP | 2002-196001 A | 7/2002 |
| JP | 2003-014764 | 1/2003 |
| JP | 2003-14764 A | 1/2003 |
| JP | 2003012709 * | 1/2003 |
| JP | 2004-163421 | 6/2004 |
| JP | 2004-163421 A | 6/2004 |
| WO | WO 91/09141 | 6/1991 |
| WO | WO 99/19000 A | 4/1999 |
| WO | WO 99/27369 | 6/1999 |
| WO | WO 02/35205 A2 | 5/2002 |
| WO | WO 03/004559 A1 | 1/2003 |

* cited by examiner

*Primary Examiner*—Shafiqul Haq
(74) *Attorney, Agent, or Firm*—Connolly Bove Lodge & Hutz LLP

(57) ABSTRACT

It is an object of the present invention to provide magnetic substance-encapsulated particles which have uniform magnetism, high dispersion stability and a narrow particle size distribution, a method of producing the same, particles for immunoassay formed by using the magnetic substance-encapsulated particles and a method of immunoassay in which the magnetic substance-encapsulated particles or the particles for immunoassay are used.

The present invention relates to a magnetic substance-encapsulated particle, which comprises an organic polymer material and a magnetic substance having an average particle size of 1 to 30 nm, the magnetic substance being contained within a particle in a state of being dispersed.

12 Claims, 1 Drawing Sheet

PARTICLE HAVING MAGNETIC MATERIAL INCORPORATED THEREIN, PROCESS FOR PRODUCING THE SAME, PARTICLE FOR IMMUNOASSAY AND METHOD OF IMMUNOASSAY

TECHNICAL FIELD

The present invention relates to magnetic substance-encapsulated particles which have uniform magnetism, high dispersion stability and a narrow particle size distribution, a method of producing the same, particles for immunoassay formed by using the magnetic substance-encapsulated particles and a method of immunoassay in which the magnetic substance-encapsulated particles or the particles for immunoassay are used.

BACKGROUND ART

Conventionally, as a method of preparing magnetic substance-containing polymer particles, there are known (1) a method of making the prepared polymer particle contain an iron ion and producing the magnetic substance, (2) a method of adding the prepared magnetic substance particle to the polymer particle in the step of polymerizing monomers (refer to Japanese Kokai Publication Hei-9-208788) and (3) a method of combining the polymer particle and the magnetic substance particle, which are separately prepared (refer to Japanese Kokai Publication Hei-6-231957). In addition to these, there is (4) a method of coating the magnetic substance particle with a polymer and the like (refer to Japanese Kokai Publication Hei-6-92640).

In the method (1), there was an issue that since the iron ion was absorbed in the polymer particle, the magnetic substance was exposed at the surface and the magnetic substance was oxidized. And, in the method (2), there was an issue that the magnetic substance particle was not uniformly taken in into the polymer particle, or an issue that the polymer particles have a wide particle size distribution since control of a particle size is difficult. And, in the method (3), there was an issue that since the polymer particles flocculate, this method cannot be applied to the case of small particle sizes. Further, in the method (4), since it is impossible to be coated uniformly, a suspending property and dispersibility are poor, and a part of the surface of a magnetic substance particle may be exposed.

On the other hand, as a method of immunoassay in a trace amount, radioimmunoassay, enzyme immunoassay and fluorescence immunoassay have been previously known and already put into practical use. Each of these methods is a method in which the antigen or the antibody, to which an isotope, an enzyme or a fluorescent material is added as a marker, is used and the presence of an antibody or an antigen, which specifically reacts with the antigen with a marker or the antibody with a marker, is detected. On the occasion of such a method of immunoassay, a magnetic substance-encapsulated particle is used in order to carry out the B/F separation efficiently and easily. And, a use other than the B/F separation (refer to Japanese Kokai Publication 2000-88852), and a method of immunoassay using the magnetic substance-encapsulated particle itself as a marker (Japanese Kokai Publication Hei-6-148189, Japanese Kokai Publication Hei-7-225233, Japanese kohyo Publication 2001-524675) are disclosed.

In a method of immunoassay in which the magnetic substance-encapsulated particle itself is used as a marker, a measuring precision thereof depends on the homogeneity of the magnetic substance-encapsulated particle, that is, the uniformity of the content of the magnetic substance in every particle. However, commercially available magnetic substance-encapsulated particles have variations in the content of the magnetic substance, and it is difficult to control the uniformity of the content of the magnetic substance by publicly known method of producing the magnetic substance-encapsulated particles.

When the magnetic substance-encapsulated particles are used for a method of immunoassay, there may be cases of handling the magnetic substance-encapsulated particles in the form of a dispersion liquid dispersed in a buffer solution and the like in a step of binding an antigen or an antibody to it or a step of mixing it with a substance to be detected. Therefore, it is desirable that the magnetic substance-encapsulated particle has such high dispersion stability that particles do not precipitate naturally in a state of a dispersion liquid. However, commercially available magnetic substance-encapsulated particles have a problem of handling that a part of the particles precipitate when they are left standing in a state of a dispersion liquid for a while, and the like.

BRIEF DESCRIPTION OF THE INVENTION

In view of the state of the art, it is an object of the present invention to provide magnetic substance-encapsulated particles which have uniform magnetism, high dispersion stability and a narrow particle size distribution, a method of producing the same, particles for immunoassay obtainable by using the magnetic substance-encapsulated particles and a method of immunoassay in which the magnetic substance-encapsulated particles or particles for immunoassay are used.

The present invention relates to a magnetic substance-encapsulated particle, which comprises an organic polymer material and a magnetic substance having an average particle size of 1 to 30 nm, the magnetic substance being contained within a particle in a state of being dispersed.

In the magnetic substance-encapsulated particle of the present invention, the absolute deviation of a component ratio between a carbon element composing the organic polymer material and a metal element composing the magnetic substance is preferably 0.3 or less.

In the magnetic substance-encapsulated particle of the present invention, the magnetic substance is preferably formed by oxidization of a metal ion within a particle in a polymerization process of forming the magnetic substance-encapsulated particle. The metal ion is preferably an iron ion.

In the magnetic substance-encapsulated particle of the present invention, a main constituent of the organic polymer material is preferably a polymer comprising an acrylic monomer, and the acrylic monomer is preferably a monomer having a glycidyl group.

And, a main constituent of the organic polymer material is preferably a polymer comprising a monomer having a glycidyl group and a styrenic monomer. In this case, the proportion of a monomer unit derived from the styrenic monomer in the organic polymer material is preferably 5 to 90% by weight.

Further, the organic polymer material preferably has polyethylene glycol (meth)acrylate represented by the following general formula (1), or a compound represented by the following general formula (2), as a monomer component:

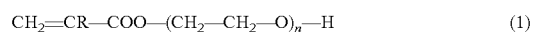  (1)

in the formula, R represents H or $CH_3$, and n represents an integer of 1 to 20,

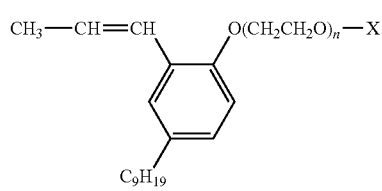

(2)

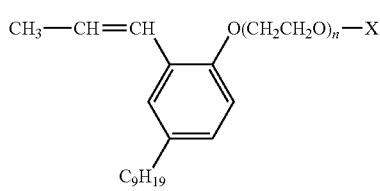

(2)

in the formula, X represents H or $SO_3^-NH_4^+$, and n represents an integer of 3 to 30. Particularly, the organic polymer material is preferably added to a monomer having a glycidyl group, or a monomer having a glycidyl group and a styrenic monomer as a copolymerization component.

In the magnetic substance-encapsulated particle of the present invention, the organic polymer material is preferably crosslinked.

The magnetic substance-encapsulated particle of the present invention preferably has at least a functional group selected from the group consisting of a carboxyl group, a hydroxyl group, an epoxy group, an amino group, a triethylammonium group, a dimethylamino group and a sulfonic acid group at the surface of the particle.

In the magnetic substance-encapsulated particle of the present invention, an average particle size is preferably 0.05 to 1 μm.

In the magnetic substance-encapsulated particle of the present invention, the content of the magnetic substance is preferably 0.1 to 50% by weight.

An average particle size of the magnetic substance contained in the magnetic substance-encapsulated particle of the present invention is preferably 2 to 10 nm.

In the magnetic substance-encapsulated particle of the present invention, it is preferred that a linker having a functional group capable of forming a covalent bond with an antigen or an antibody binds to a particle surface. The functional group is preferably an epoxy group and the linker is preferably polyethylene glycol diglycidyl ether.

The magnetic substance-encapsulated particle of the present invention is produced by a method comprising the steps of: polymerizing a monomer not having a hydrophilic group and/or a monomer having a hydrophilic group in a water solvent to form a particle; and oxidizing a metal ion while taking in the metal ion into the particle to form a magnetic substance, the step of forming a particle and the step of forming a magnetic substance being simultaneously performed.

The monomer not having a hydrophilic group is preferably an acrylic monomer having a glycidyl group, or an acrylic monomer having a glycidyl group and a styrenic monomer. And, it is preferred that a particle is formed by polymerizing a monomer not having a hydrophilic group and a monomer having a hydrophilic group, and the monomer having a hydrophilic group is polyethylene glycol (meth)acrylate represented by the following general formula (1) or a compound represented by the following general formula (2):

$$CH_2=CR-COO-(CH_2-CH_2-O)_n-H \qquad (1)$$

in the formula, R represents H or $CH_3$, and n represents an integer of 1 to 20, in the formula, X represents H or $SO_3^-NH_4^+$, and n represents an integer of 3 to 30.

And, in the step of forming a particle, a reactive emulsifier may be added as a copolymerization monomer. And, it is preferred that polymerization initiator is added afterward.

A particle for immunoassay, which is obtainable by adsorbing or binding an antigen or an antibody to the magnetic substance-encapsulated particle of the present invention, also constitutes the present invention.

And, a method of immunoassay, wherein the magnetic substance-encapsulated particle or the particle for immunoassay of the present invention is used, also constitutes the present invention.

Further, a method of immunoassay, wherein the magnetic substance-encapsulated particle of the present invention is used as a marker, also constitutes the present invention.

In the method of immunoassay of the present invention, an immuno chromatogram method is preferably used.

DETAILED DESCRIPTION OF THE INVENTION

Figure 1:
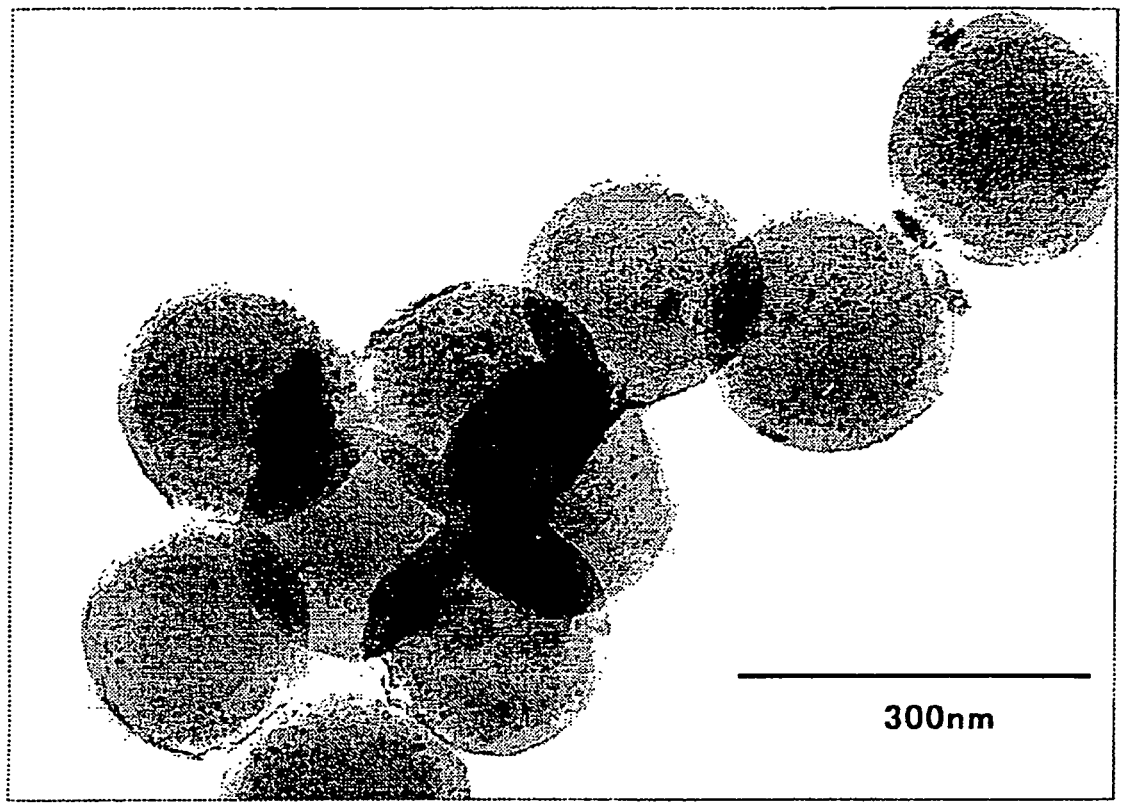
FIG. 1 shows a TEM photograph of magnetic substance-encapsulated particles (average particle sizes; 0.21 μm of magnetic substance-encapsulated particles, 5 nm of magnetic substances) obtained in Example 2.

Hereinafter, the present invention will be described in detail.

A magnetic substance-encapsulated particle of the present invention comprises an organic polymer material and a magnetic substance having an average particle size of 1 to 30 nm.

A main constituent of the organic polymer material is a polymer comprising a monomer not having a hydrophilic group for forming a core of a particle and a monomer having a hydrophilic group for forming a shell of a particle while forming a particle having the dispersion stability in water.

<Monomer not Having a Hydrophilic Group>

As the monomer not having a hydrophilic group, there are given, for example, styrenic monomers such as styrene, α-methylstyrene, p-methylstyrene, p-chlorostyrene, chloromethylstyrene; vinyl esters such as vinyl chloride, vinyl acetate, vinyl propionate; unsaturated nitriles such as acrylonitrile; and acrylic monomers such as methyl (meth)acrylate, ethyl(meth)acrylate, butyl(meth)acrylate, 2-ethylhexyl (meth)acrylate, stearyl(meth)acrylate, ethylene glycol(meth) acrylate, trifluoroethyl (meth)acrylate, pentafluoropropyl (meth)acrylate, cyclohexyl(meth)acrylate, glycidyl(meth) acrylate, tetrahydrofurfuryl(meth)acrylate. These monomers not having a hydrophilic group may be used alone or in combination of two or more species.

As the monomers not having a hydrophilic group, there are preferably used acrylic monomers such as methyl (meth) acrylate, ethyl(meth)acrylate, butyl(meth)acrylate, 2-ethylhexyl(meth)acrylate, stearyl(meth)acrylate, ethylene glycol (meth)acrylate, trifluoroethyl (meth)acrylate, pentafluoropropyl(meth)acrylate, cyclohexyl(meth)acrylate, glycidyl(meth)acrylate, tetrahydrofurfuryl(meth)acrylate, etc.

As the monomer not having a hydrophilic group, there are more preferably used acrylic monomers having a glycidyl group which have the excellent capability of taking in metal ions in high concentrations during polymerizing particles in order to simultaneously perform forming a particle and forming a magnetic substance by polymerization. Among the acrylic monomers, glycidyl methacrylate (GMA) is particularly suitably used because of a high affinity for iron ions and magnetite.

And, it is preferred to use the acrylic monomer having a glycidyl group and a styrenic monomer in combination.

When the acrylic monomer having a glycidyl group and the styrenic monomer are used in combination as the monomer not having a hydrophilic group, the proportion of a monomer unit derived from the styrenic monomer in the organic polymer material is preferably 5 to 90% by weight. When the proportion is less than 5% by weight, the dispersion stability of the obtained particles in water becomes low and the particles becomes apt to self-flocculate, and when it is more than 90% by weight, an affinity for metal ions which are precursor of the magnetic substance becomes low and an amount of the magnetic substance to be formed within a particle becomes small.

When the acrylic monomer having a glycidyl group and the styrenic monomer are used in combination, methyl methacrylate may be further used in combination.

And, in some uses, a crosslinkable monomer may be used as the monomer not having a hydrophilic group, and the organic polymer material may be crosslinked.

The crosslinkable monomer includes, for example, divinylbenzene, divinylbiphenyl, divinylnaphthalene, ethylene glycol di(meth)acrylate, 1,6-hexanediol di(meth)acrylate, neopentyl glycol di(meth)acrylate, trimethylolpropane tri(meth)acrylate, tetramethylolmethane tri(meth)acrylate, tetramethylolpropane tetra(meth)acrylate, diallyl phthalate and isomer thereof, and triallyl isocyanurate and isomer thereof. These crosslinkable monomers may be used alone or in combination of two or more species.

Among these crosslinkable monomers, ethylene glycol di(meth)acrylate is suitably used because of a high affinity for iron ions and magnetite.

<Monomers Having a Hydrophilic Group>

As the monomers having a hydrophilic group, there are given, for example, carboxylic acids having a polymerizable unsaturated bond such as acrylic acid, methacrylic acid, itaconic acid, fumaric acid, maleic acid; phosphate esters having a polymerizable unsaturated bond; sulfonate esters having a polymerizable unsaturated bond; vinyl-based monomers having a cation group, like amine salts having an acryloyl group, such as quaternary salt of dimethylaminoethyl methacrylate and quaternary salt of diethylaminoethyl methacrylate, and salts of nitrogen-containing compound having a vinyl group, such as vinylpyridine; substances generally called the hydrophilic monomer like nonionic vinyl-based monomer such as 2-hydroxyethyl methacrylate, polyethylene glycol (meth)acrylate, (meth)acrylamide, methylolacrylamide, glycerol methacrylate (GLM); and in addition reactive emulsifier having a hydrophilic group. These monomers having a hydrophilic group may be used alone or in combination of two or more species.

As the reactive emulsifier having a hydrophilic group, there are given, for example, reactive emulsifiers represented by the following general formulas (2) to (9).

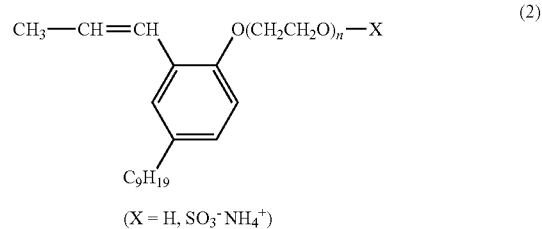

(X = H, SO$_3^-$NH$_4^+$)

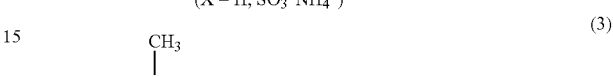

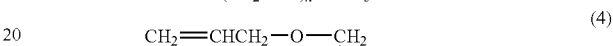

(X = H, SO$_3^-$NH$_4^+$)

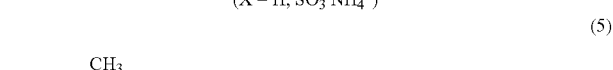

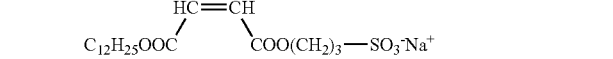

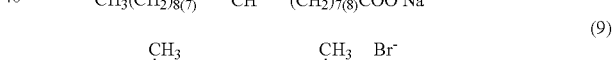

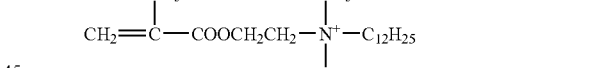

Particularly in the monomer having a hydrophilic group, polyethylene glycol(meth)acrylate represented by the following general formula (1), or a reactive emulsifier represented by the general formula (2) is suitably used since they have the high capability of dispersing particles stably in water and does not interfere with the formation of the magnetic substance.

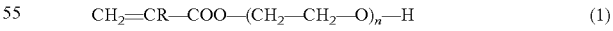

in the formula, R represents H (hydrogen) or CH$_3$ and n represents an integer of 1 to 20.

In the general formula (2), n represents an integer of 3 to 30 and preferably represents an integer of 5 to 20.

The magnetic substance-encapsulated particles of the present invention preferably have small variations in the content of the magnetic substance. As a method of evaluating the variations in the content of the magnetic substance of the magnetic substance-encapsulated particle, there are given a method of employing SEM-EDX and a method of using synchronous luminescence analysis.

The SEM-EDX is an apparatus which perform an EDX analysis (a qualitative analysis, a quantitative analysis, mapping, a particle analysis and the like) of a microarea which is observed with a SEM and can measure the variations in the content of the magnetic substance.

As a measuring apparatus using the synchronous luminescence analysis, for example, a particle analyzer (DP-1000, manufactured by HORIBA, Ltd.) is commercially available. This particle analyzer has a mechanism of irradiating high excited energy of microwave induced helium plasma to solid fine particles sampled by an aspirator and measuring synchronous luminescence of every solid fine particle and can analyze a wide range of elements of the solid fine particle and a state in which various components exist and are mixed.

Variations in the content of the magnetic substance of the magnetic substance-encapsulated particles can be compared and evaluated using a deviation (absolute deviation) indicating the variance of measurement data, derived from variations in a component ratio between a carbon element and a metal element in a particle, which are determined by measuring synchronous luminescence of a carbon element composing the organic polymer material and a metal element composing the magnetic substance. It is shown that variations in the content of the magnetic substance decrease, that is, the uniformity of the magnetic substance-encapsulated particle is enhanced as the value of the deviation decreases and variations in the content of the magnetic substance increase, that is, the uniformity of the magnetic substance-encapsulated particle is deteriorated as the value of the deviation increases.

With respect to the magnetic substance-encapsulated particles of the present invention, the absolute deviation of a component ratio between a carbon element composing the organic polymer material and a metal element composing the magnetic substance is preferably 0.3 or less. If the absolute deviation is more than 0.3, the reproducibility and the quantitative level of measurement are reduced, a measuring accuracy becomes poor and the reliability of the obtained measurement data is deteriorated when the magnetic substance-encapsulated particle is used in a method of immunoassay. The absolute deviation is more preferably 0.27 or less, furthermore preferably 0.25 or less and furthermore preferably 0.20 or less.

The magnetic substance is preferably formed by oxidization of a metal ion within a particle in a polymerization process of forming the magnetic substance-encapsulated particle.

<Metal Ion>

The metal ion is not particularly limited as long as it is a substance to form the magnetic substance, but it is preferably an iron ion, a cobalt ion, a nickel ion and the like, and more preferably an iron ion. Magnetite, a magnetic substance, is obtained by oxidizing ferric chloride with an oxidizing agent and the like. The magnetic substance (magnetite)-encapsulated particle is prepared by initiating the polymerization of the monomer described with an initiator and simultaneously oxidizing a bivalent iron ion (converting to magnetite).

The magnetic substance has an average particle size of 1 to 30 nm. When the average particle size is less than 1 nm, a characteristic of magnetic response of the magnetic substance is reduced, that is, a characteristic of magnetic response of the magnetic substance-encapsulated particle is reduced and measuring sensitivity in using for immunoassay is deteriorated. And, when it is more than 30 nm, the dispersibility of the magnetic substance in a particle is deteriorated. The average particle size is preferably 2 to 20 nm, and more preferably 2 to 10 nm.

In the magnetic substance-encapsulated particles of the present invention, the magnetic substance is contained within the magnetic substance-encapsulated particle in a state of being dispersed. That is, in the magnetic substance-encapsulated particles of the present invention, the magnetic substance exists in a state of being dispersed within a particle without being exposed at the surface of a particle.

The content of the magnetic substance of the magnetic substance-encapsulated particles of the present invention is preferably adjusted in the range of 0.1 to 50% by weight. When this content is less than 0.1% by weight, a characteristic of magnetic response of the magnetic substance-encapsulated particle is reduced and measuring sensitivity in using for immunoassay is deteriorated. And, when it is more than 50% by weight, the operability of polymerizing particles is deteriorated and it become difficult to take in metal ions during polymerizing particles. It is more preferably 0.1 to 40% by weight, and furthermore preferably 1 to 30% by weight.

And, the magnetic substance-encapsulated particle of the present invention may have functional groups such as a carboxyl group, a hydroxyl group, an epoxy group, an amino group, a triethylammonium group, a dimethylamino group and a sulfonic acid group at the surface thereof as required. The magnetic substance-encapsulated particle can form a covalent bond with the antigen or the antibody via these functional groups.

The functional group can be introduced at the surface of the magnetic substance-encapsulated particle by previously mixing monomers having respective functional groups in a mixture of monomers for polymerization or by adding monomers having respective functional groups during polymerizing. With respect to the monomer having the functional groups, a monomer having a carboxyl group includes (meth)acrylic acid and the like, a monomer having a hydroxyl group includes 2-hydroxyethyl(meth)acrylate and the like, a monomer having an epoxy group includes glycidyl (meth)acrylate and the like, a monomer having a triethylammonium group includes triethylammonium(meth)acrylate and the like, and a monomer having a dimethylamino group includes dimethylamino (meth)acrylate and the like.

In the magnetic substance-encapsulated particle of the present invention, a linker having a functional group capable of forming a covalent bond with an antigen or an antibody may bind to a particle surface as required.

<Linker>

The linker is a chemical material which exists between the particle comprising an organic polymer material and a compound such as an antigen and an antibody in using the magnetic substance-encapsulated particle for immunoassay. It is preferred that the linker has a length of not causing the steric hindrance and is a compound in which a nonspecific adsorption hardly occurs and has a functional group, such as an amino group, a carboxyl group, an epoxy group, a tosyl group and a thiol group, capable of forming a covalent bond with an antigen or an antibody at its molecule end before binding to the particle comprising an organic polymer material and the compound such as an antigen and an antibody. The linker in the present invention is not particularly limited as long as it can bind an epoxy group derived from a glycidyl group-containing monomer, a hydroxyl group produced by ring opening of an epoxy group, or an amino group at the surface of particle and an antigen, an antibody and the like putting adequate distance between them. Preferably, there are given compounds having epoxy groups at a plurality of ends, for example, polyethylene glycol diglycidyl ether, polypropylene glycol diglycidyl ether, neopentyl glycol diglycidyl ether and trimethylolpropane polyglycidyl ether. More preferably, there is given polyethylene glycol diglycidyl ether.

By introducing such a linker at the particle surface of the magnetic substance-encapsulated particle, it becomes possible to enhance the reactivity of, for example, an antigen, an antibody or an agent to bind to the magnetic substance-encapsulated particle, that is, a sensitive and precise measurement becomes possible, and even when the particle surface of the magnetic substance-encapsulated particle is non-adsorbent against protein, it becomes possible to bind the antigen or the antibody to the magnetic substance-encapsulated particle with reliability because the linker has a binding property to protein.

An average particle size of the magnetic substance-encapsulated particles of the present invention is preferably adjusted in the range of 0.05 to 1 μm depending on its polymerizing conditions. When the average particle size is less than 0.05 μm, the particles becomes apt to self-flocculate and the dispersion stability becomes low, and when it is more than 1 μm, for example in the case of using the magnetic substance-encapsulated particle in a suspension, the magnetic substance-encapsulated particle becomes apt to precipitate, and in the case of using the magnetic substance-encapsulated particle in a porous carrier as with an immuno chromatogram method, the magnetic substance-encapsulated particle becomes hard to move in the porous carrier and therefore handeability of an agent is deteriorated. It is more preferably 0.06 to 0.8 μm, and furthermore preferably 0.07 to 0.5 μm.

The magnetic substance-encapsulated particle of the present invention is produced by a method comprising the steps of: polymerizing the monomer not having a hydrophilic group and/or the monomer having a hydrophilic group in a water-based solvent to form a particle; and oxidizing a metal ion while taking in the metal ion into the particle to form a magnetic substance, the step of forming a particle and forming a magnetic substance are simultaneously performed.

In the step of polymerizing the monomer not having a hydrophilic group and/or the monomer having a hydrophilic group in a water-based solvent to form a particle, a polymerization initiator is used.

<Polymerization Initiator>

The initiator is not particularly limited and includes, for example, water-soluble organic azo compounds, inorganic peroxides and organic peroxides.

As a suitable example of the polymerization initiator, there are given potassium persulfate (hereinafter, referred to as "KPS"; polymerizing temperature 70° C.), azobis amidinopropane hydrochloride (polymerizing temperature 70° C.), 2,2-azobis[2-(2-imidazoline-2-yl)propane]dihydrochloride (polymerizing temperature 60° C.) and ammonium persulfate (polymerizing temperature 70° C.) and the like. Among these compound, KPS or ammonium persulfate, peroxide type polymerization initiator, is expected to contribute to the oxidation of bivalent iron ion concurrently with the initiation of polymerization. When KPS or ammonium persulfate is used, it is assumed that polymerization and formation of magnetite by a monomer and an iron ion are performed concurrently. Azobis amidinopropane hydrochloride and 2,2-azobis[2-(2-imidazoline-2-yl)propane]dihydrochloride are low in an oxidizing power and become a polymerization initiator participating in a mild oxidation reaction of bivalent iron ion. In addition, as azobis amidinopropane hydrochloride, "V-50 (trade name)" (produced by Wako Pure Chemical Industries, Ltd.) is commercially available, and as 2,2-azobis[2-(2-imidazoline-2-yl)propane]dihydrochloride, "VA-044 (trade name)" (produced by Wako Pure Chemical Industries, Ltd.) is commercially available.

Since the polymerization initiator can be consumed in oxidation of $Fe^{2+}$ or lose its radical activity due to $Fe^{3+}$, it is effective to add afterward the polymerization initiator in a process of the growth of particle for the purpose of growing the particle. In this case, secondary particles are not newly formed and the surface of particle is coated with a polymer.

<pH Adjustment Agent>

In the present invention, in order to prepare the magnetic substance concurrently with polymerization, a pH in the polymerization system is preferably adjusted to be basic. In a system in which KPS or ammonium persulfate is used as the polymerization initiator, there is a merit that the dispersion stability in water is high and the monodisperse particles having a narrow particle size distribution are obtained, but there is a demerit that the particles are weakly attracted to a magnet since an oxidizing power cannot be controlled and the inside of the polymerization system becomes acidic. On the other hand, a system in which 2,2-azobis[2-(2-imidazoline-2-yl)propane]dihydrochloride not having an oxidizing power is used as the polymerization initiator has a merit that a pH in a polymerization system is substantially neutral.

In order to keep a pH in the polymerization system weakly basic, general basic compounds can be used. $NH_4OH$ is preferably used as a pH adjustment agent.

The pH adjustment agent can be added several times as required.

<Method of Polymerization>

The magnetic substance-encapsulated particles of the present invention can be produced by methods of polymerizing particles, such as suspension polymerization, dispersion polymerization, emulsion polymerization and soap free emulsion polymerization, but they are suitably produced by soap free emulsion polymerization which is superior in controlling a particle size distribution since Cv value of the magnetic substance-encapsulated particles ultimately obtained is preferably 5% or less.

Hereinafter, a method of producing the magnetic substance-encapsulated particle by soap free emulsion polymerization is exemplified, but the method of polymerization is not limited to this method.

Typical polymerization composition comprising:
a monomer composition comprising a monomer having a hydrophilic group and a monomer not having a hydrophilic group: 3 g; and
$H_2O$: 100 gram. The monomer composition and water are weighed and put into a four-necked flask. A stirring rod and a reflux cooling tube are attached to the respective necks. Next, this system is put in a thermostatic chamber and the inside of the system is replaced with nitrogen gas while stirring the contents of the flask. The temperature of the thermostatic chamber is preferably adjusted to a polymerizing temperature of a polymerization initiator to be added, and preferably adjusted to 70° C., for example, when using KPS, azobis amidinopropane hydrochloride or ammonium persulfate as a polymerization initiator, and preferably adjusted to from 50 to 60° C. when using 2,2-azobis[2-(2-imidazoline-2-yl)propane]dihydrochloride as a polymerization initiator. Then, a polymerization initiator dissolved in water is injected in the system with an injection cylinder. This time of injection is assumed to be the initiation of polymerization, and after a predetermined amount of time, an water solution of $FeCl_2 \cdot 4H_2O$ to become a magnetic source is injected in the flask with an injection cylinder. As FeCl$_2$.4H$_2$O, there is used a solution obtainable by dissolving FeCl$_2$.4H$_2$O in an amount of ⅓-times to 4-times in mole as much as that of the polymerization initiator in 5 g of water. That is, the particle is produced by initiating the polymerization of the monomer described and simultaneously oxidizing a bivalent iron ion (converting to magnetite) by virtue of a polymerization initiator.

It is preferred to continue polymerization for 2 to 24 hours from the initiation of polymerization. NH$_4$OH may be added during polymerizing in order to attain adequate oxidizing power, and further a polymerization initiator may be added during polymerizing in order to promote the growth of a particle by polymerization. Thus, a particle comprising an organic polymer material containing the magnetic substance in a state of being dispersed can be obtained.

A reactive emulsifier may be added to the monomer composition as a copolymerization monomer.

<Reactive Emulsifier>

As the reactive emulsifier, there are given reactive emulsifiers represented by, for example, the following general formulas (2) to (10).

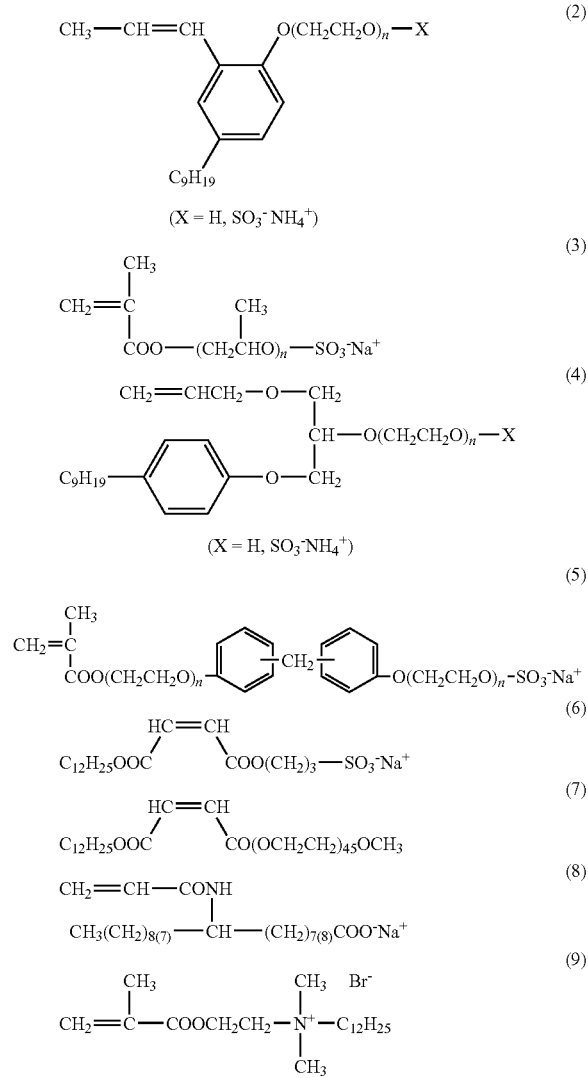
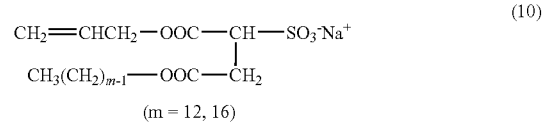

These reactive emulsifiers may be used alone or in combination of two or more species. Prepared particles are purified by repeating the operations of centrifugal separation/re-dispersion using distilled water in order to remove a residual monomer, an initiator, an unreacted iron ion and the like. After the centrifugal separation, supernatant liquid is taken off by decantation, and distilled water is added, and the particles are re-dispersed with a glass rod. After the purification, the obtained magnetic substance-encapsulated particles are transferred into a glass vial, sealed with a lid and a paraffin film and stored.

Introduction of a linker at the particle surface of the magnetic substance-encapsulated particle of the present invention can be carried out, for example, by dispersing magnetic substance-encapsulated particles, at which a linker is not yet introduced, in an alkaline water solution, subsequently adding a chemical compound to become a linker, such as polyethylene glycol diglycidyl ether, and mixing the resulting mixture for about 24 hours.

Since the magnetic substance-encapsulated particles of the present invention thus obtained have a narrow particle size distribution and small variations in the content of the magnetic substance, they are extremely homogeneous. Therefore, the magnetic substance-encapsulated particles of the present invention have high dispersion stability and excellent handleability. And, since the magnetic substance-encapsulated particles of the present invention have a relatively small average particle size, they have good colloid stability. And, since in the magnetic substance-encapsulated particle of the present invention, the encapsulated magnetic substances are dispersed in a minute size and contained in a particle, there is no residual magnetism even when the magnetic substance is magnetized and the precipitation due to self-flocculation resulting from the residual magnetism does not occur.

By adsorbing or bonding an antigen or an antibody to the magnetic substance-encapsulated particle of the present invention, particles for immunoassay can be obtained. As a method of adsorbing or bonding an antigen or an antibody to the magnetic substance-encapsulated particle, there can be employed publicly known methods such as a physical adsorption method and a chemical bonding method using carbodiimide. When a linker having an epoxy group is introduced at the particle surface of the magnetic substance-encapsulated particle of the present invention, particles for immunoassay can be prepared by chemically bonding the magnetic substance-encapsulated particle to an amino group or a thiol group of the antigen or the antibody via a linker. Such particles for immunoassay obtainable by binding an antigen or an antibody to the magnetic substance-encapsulated particles of the present invention also constitute the present invention.

The magnetic substance-encapsulated particles and particles for immunoassay of the present invention can be used for a method of immunoassay. A method of immunoassay, in which the magnetic substance-encapsulated particles or the particles for immunoassay of the present invention are used, also constitutes the present invention.

As the method of immunoassay of the present invention, there are given publicly known methods such as radioimmunoassay and enzyme immunoassay which use magnetic substance-encapsulated particles as a carrier, and an objective antigen or antibody can be measured by a competition method or a sandwich method. The magnetic substance-encapsulated particle can be used as a marker in place of an isotope, an enzyme and the like which are marker materials of the method. Since the magnetic substance-encapsulated particles of the present invention are particles with a narrow particle size distribution, which contain the magnetic substance dispersed uniformly, by using it as a marker in the method of immunoassay, a sensitive and precise measurement can be performed.

As the specific example of the method of immunoassay in which the magnetic substance-encapsulated particles of the present invention are used as a marker, there are given a method of immunoassay in which a fluorescent material, a colored particle, a metal colloid and the like have been previously utilized as a marker. Among others, an immuno chromatogram method, which is often used as a method detecting materials to be detected easily and promptly in recent years, is suitable. In the immuno chromatogram method, a sandwich method using at least two species of antibodies is employed. In the sandwich method, one antibody is marked in a state of being movable in a liquid phase and the other antibody is permanently fixed to a chromatogram carrier. When a sample is added to an agent of the sandwich method, first, the marked antibody reacts with a substance to be detected, and then a complex of the marked antibody and the substance to be detected moves through a chromatogram carrier, and when the complex reaches a fixation point where the other antibody is fixed to a chromatogram carrier, the complex is trapped there by the fixed antibody. Generally, a chromatogram carrier to be used in the immuno chromatogram method has a pore size of 5 to 20 μm, and currently, a general sandwich method is used as a qualitative examination in which a metal colloid or a colored particle is used as a marker and coloring of a fixation point (trapping state of a marked substance) is visually observed.

However, since commercially available magnetic substance-encapsulated particles have the problems that they are retained in a chromatogram carrier or remain nonuniformly around a tip portion of chromatogram which is the side of letting the particles develop and have an extremely lower chromatogram developing property in comparison with a metal colloid or a colored particle, they do not have the suitability for the immuno chromatogram method.

On the other hand, since the magnetic substance-encapsulated particles of the present invention have an adequately small particle size compared with the pore size, these particles can develop (move) in a chromatogram carrier by virtue of a capillary phenomenon. That is, when the magnetic substance-encapsulated particle of the present invention is developed in a chromatogram carrier having an average pore size (10 to 12 μm), nonuniform retention described was not found and a chromatogram developing property is very excellent. The reason is assumed to be that the magnetic substance-encapsulated particles of the present invention (1) have the narrow particle size distribution, (2) have the uniform content of the magnetic substance and (3) does not cause the self-flocculation due to residual magnetism. That is, the magnetic substance-encapsulated particles of the present invention have the suitability for the immuno chromatogram method in contrast to the conventional magnetic substance-encapsulated particles.

BEST MODE FOR CARRYING OUT THE INVENTION

Hereinafter, the present invention will be described in more detail by way of examples, but the present invention is not limited to these examples.

EXAMPLES 1 to 7

The respective monomers shown in Table 1 and 90 g of water were put into a two hundreds milliliter, four-necked flask. A stirring seal/a stirring rod, a reflux cooling tube and CERAM rubber were attached to the respective necks. This system was put in a thermostatic chamber of 70° C. and the inside of the system was replaced with nitrogen gas for 30 minutes while stirring the contents of the flask at a rotational speed of 200 rpm. Then, 0.06 g of KPS which is a polymerization initiator dissolved in water was dissolved in 10 g of water and the resulting solution was injected in the system with an injection cylinder. This time of injection was assumed to be the initiation time of polymerization, and a water solution of $NH_4OH$ (obtainable by dissolving 0.165 g of $NH_4OH$ in 5 g of water) was added to the mixture in the flask during polymerizing in order to attain adequate oxidizing power. And, after a lapse of two minutes from the initiation of polymerization, a water solution of $FeCl_2.4H_2O$ (obtainable by dissolving 0.165 g of $FeCl_2.4H_2O$ in 5 g of water) was injected in the flask with an injection cylinder. Polymerization was continued for 20 hours from the initiation of polymerization.

Prepared particles were purified by repeating the operations of centrifugal separation/re-dispersion fourth times using distilled water. In this time, the centrifugal separation was conducted at 20° C. and at rotational speed of 13500 rpm. After the centrifugal separation, supernatant liquid was taken off by decantation, and distilled water was added, and the particles were re-dispersed with a glass rod to obtain magnetic substance-encapsulated particles.

TABLE 1

| Example | GMA | EGDM | AAm | PE-90 | PE-350 | NE-20 | SE-20 | $FeCl_2 \cdot 4H_2O$ |
|---|---|---|---|---|---|---|---|---|
| 1 | 2.835 | 0.015 | 0.15 | — | — | — | — | 0.088 |
| 2 | 2.835 | 0.015 | — | 0.15 | — | — | — | 0.176 |
| 3 | 2.685 | 0.015 | — | 0.3 | — | — | — | 0.176 |
| 4 | 2.835 | 0.015 | — | — | 0.15 | — | — | 0.176 |
| 5 | 2.685 | 0.015 | — | — | 0.3 | — | — | 0.176 |
| 6 | 2.835 | 0.015 | 0.05 | — | — | 0.15 | — | 0.088 |
| 7 | 2.835 | 0.015 | 0.15 | — | — | — | 0.06 | 0.176 |

(unit: g)

An explanation of abbreviations in Table 1 is as follows.
GMA: glycidyl methacrylate
EGDM: ethylene glycol dimethacrylate
AAm: acrylamide
PE-90: polyethylene glycol methacrylate (n=2)
PE-350: polyethylene glycol methacrylate (n=8)
NE-20:

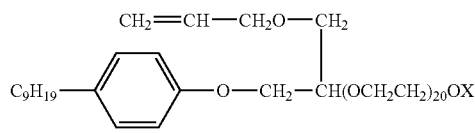

in the formula, X represents H (hydrogen).
SE-20:

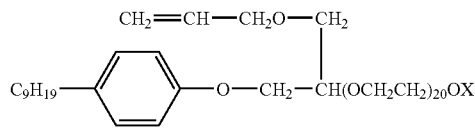

in the formula, X represents $SO_4NH_4$.

On the obtained dispersion liquid of the magnetic substance-encapsulated particles, a state of dispersion was visually observed. And, purified magnetic substance-encapsulated particles were diluted with water and deposited and fixed on a collodion membrane supported by a metal mesh, and the shape of the particles was observed with a transmission electron microscope (TEM).

The magnetic substance-encapsulated particles obtained in Example 1 were re-dispersed through ultrasonic treatment since they had such rather low dispersion stability that flocculates of particles were partially found and the magnetic substance-encapsulated particles precipitated with time. On the other hand, in Examples 2 to 5 in which polyethylene glycol meth acrylate was used as a monomer having a hydrophilic group, and in Examples 6 and 7 in which a reactive emulsifier was used, any flocculates were not found and the magnetic substance-encapsulated particles having high dispersion stability could be obtained. Particularly, the magnetic substance-encapsulated particles obtained in Examples 6 and 7, in which the reactive emulsifier was used, were found to have small particle sizes and high dispersion stability. And, it was observed that each of the magnetic substance-encapsulated particles obtained in Examples 1 to 7 contained the magnetic substance within the magnetic substance-encapsulated particle in a state of being dispersed and had a particle surface of a clear outline. A TEM photograph of magnetic substance-encapsulated particles (average particle sizes; 0.21 μm of magnetic substance-encapsulated particles, 5 nm of magnetic substances) in Example 2 is shown in FIG. 1. And, average particle sizes of the magnetic substances of the magnetic substance-encapsulated particles in Examples 1 to 7 are shown in Table 2.

TABLE 2

| Example | Average particle size (nm) |
|---|---|
| 1 | 5 |
| 2 | 5 |
| 3 | 6 |

TABLE 2-continued

| Example | Average particle size (nm) |
|---|---|
| 4 | 6 |
| 5 | 8 |
| 6 | 3 |
| 7 | 5 |

Further, in order to verify that the magnetic substance-encapsulated particles prepared in Examples 1 to 7 are attracted to a magnet, a small amount of a dispersion liquid of the magnetic substance-encapsulated particle was put in a 1.5 ml microtube and appropriately diluted with distilled water, and the microtube was stood up on a microtube-stand (manufactured by DYNAL BIOTECH, MPC (registered trademark)-M) and it was visually observed that the dispersed magnetic substance-encapsulated particles were attracted to a magnet. It was discernible that particularly, magnetic substance-encapsulated particles of Examples 2 to 5, in which polyethylene glycol methacrylate was used as a monomer having a hydrophilic group, had a larger magnetic force than that of other Examples 1, 6 and 7.

EXAMPLE 8

The respective monomers and water shown below were put into a two hundreds milliliter, four-necked flask. GMA/EGDM/AAm/$H_2O$=2.835/0.015/0.15/90 (unit: g)

A stirring seal/a stirring rod, a reflux cooling tube and CERAM rubber were attached to the respective necks. This system was put in a thermostatic chamber of 70° C. and the inside of the system was replaced with nitrogen gas for 30 minutes while stirring the contents of the flask at a rotational speed of 200 rpm. Then, 0.06 g of KPS which is a polymerization initiator dissolved in water was dissolved in 10 g of water and the resulting solution was injected in the system with an injection cylinder. This time of injection was assumed to be the initiation time of polymerization, and a water solution of $NH_4OH$ (obtainable by dissolving 0.165 g of $NH_4OH$ in 5 g of water) was added to the mixture in the flask after a lapse of one minute from the initiation of polymerization in order to attain adequate oxidizing power. And, after a lapse of two minutes from the initiation of polymerization, a water solution of $FeCl_2.4H_2O$ (obtainable by dissolving 0.165 g of $FeCl_2.4H_2O$ in 5 g of water) was injected in the flask with an injection cylinder. Polymerization was continued for 2 hours from the initiation of polymerization.

Prepared particles were purified by repeating the operations of centrifugal separation/re-dispersion four times using distilled water. In this time, the centrifugal separation was conducted at 20° C. and at rotational speed of 13500 rpm. After the centrifuge separation, supernatant liquid was taken off by decantation, and distilled water was added, and the particles were re-dispersed with a glass rod to obtain magnetic substance-encapsulated particles.

EXAMPLE 9

Magnetic substance-encapsulated particles were obtained by following the same procedure as in Example 8 except for changing the addition timing of the following substances after the initiation of polymerization to the following specified time and changing the polymerizing time to 3 hours from the initiation of polymerization.

A water solution of NH$_4$OH (obtainable by dissolving 0.165 g of NH$_4$OH in 5 g of water): after a lapse of 30 minutes from the initiation of polymerization KPS (obtainable by dissolving 0.165 g of KPS in 5 g of water): after a lapse of 60 minutes from the initiation of polymerization

EXAMPLE 10

Magnetic substance-encapsulated particles were obtained by following the same procedure as in Example 8 except for changing the addition timing of the following substances after the initiation of polymerization to the following specified time, adding GMA further afterward and changing the polymerizing time to 3 hours from the initiation of polymerization.

KPS (obtainable by dissolving 0.165 g of KPS in 5 g of water): after a lapse of 60 minutes from the initiation of polymerization A water solution of FeCl$_2$.4H$_2$O (obtainable by dissolving 0.165 g of FeCl$_2$-4H$_2$O in 5 g of water): after a lapse of 60 minutes from the initiation of polymerization GMA 0.5 g: after a lapse of 120 minutes from the initiation of polymerization (further, 2.835 g of GMA was put into the four-necked flask before the initiation of polymerization as with Example 8)

A water solution of NH$_4$OH (obtainable by dissolving 0.165 g of NH$_4$OH in 5 g of water): after a lapse of 120 minutes from the initiation of polymerization

EXAMPLE 11

Magnetic substance-encapsulated particles were obtained by following the same procedure as in Example 8 except for changing the addition timing of the following substances after the initiation of polymerization to the following specified time and changing the polymerizing time to 4 hours from the initiation of polymerization.

A water solution of NH$_4$OH (obtainable by dissolving 0.165 g of NH$_4$OH in 5 g of water): after a lapse of one minute from the initiation of polymerization KPS (obtainable by dissolving 0.165 g of KPS in 5 g of water): after a lapse of 120 minutes from the initiation of polymerization On the magnetic substance-encapsulated particles obtained in Examples 8 to 11, the shape of the magnetic substance-encapsulated particles was observed in the same way as in Example 1 using a TEM.

It was recognized that both magnetic substance-encapsulated particles obtained in Examples 9 and 10 contained a larger amount of the magnetic substance than that in Example 8 and increased in particle sizes. And, in Example 11, it was observed that the magnetic substance-encapsulated particle contained the magnetic substance in an amount similar to that in Examples 9 and 10 within a particle and had a particle surface of a clear outline.

From the experiments, it was assumed that the addition of NH$_4$OH at the early stage of particle-growth becomes a cause of inhibiting the growth of particles. On the other hand, in the case of adding a polymerization initiator afterward, a percentage of polymerization is nearly 100%, and it was observed that secondary particles were not formed and the surface of particle was coated with a polymer, and therefore it was verified that addition of a polymerization initiator afterward was effective method. Average particle sizes of the magnetic substances in the magnetic substance-encapsulated particles in Examples 8 to 11 are shown in Table 3.

TABLE 3

| Example | Average particle size (nm) |
|---------|---------------------------|
| 8  | 8  |
| 9  | 8  |
| 10 | 10 |
| 11 | 8  |

EXAMPLE 12

1.0 g of the magnetic substance-encapsulated particle obtained in Example 2 was added to 50 ml of 10% ammonia water and the mixture was stirred at 70° C. for 20 hours. Next, centrifugal washing of the particles was conducted three times using ion-exchanged water and the particles were dispersed in 50 ml of ion-exchanged water. Subsequently, 30 g of ethylene glycol diglycidyl ether was added to this dispersion liquid and mixed, and the mixture was adjusted to pH 11 using a water solution of sodium hydroxide, and then stirred at room temperature for 24 hours. After a reaction, centrifugal washing of a reactant was conducted three times using ion-exchanged water to obtain magnetic substance-encapsulated particles to each of which a linker having an epoxy group was bound.

EXAMPLE 13

3.0 g of styrene, 3.0 g of glycidyl methacrylate, 0.03 g of ethylene glycol dimethacrylate, 0.3 g of polyethylene glycol methacrylate and 200 g of water were put into a two hundreds milliliter, four-necked flask. A stirring seal/a stirring rod, a reflux cooling tube and CERAM rubber were attached to the respective necks. This system was put in a thermostatic chamber of 70° C. and the inside of the system was replaced with nitrogen gas for 30 minutes while stirring the contents of the flask at a rotational speed of 200 rpm. Then, 0.1 g of KPS which is a polymerization initiator dissolved in water was dissolved in 20 g of water and the resulting solution was injected in the system with an injection cylinder. This time of injection was assumed to be the initiation time of polymerization, and after a lapse of two minutes, a water solution of FeCl$_2$.4H$_2$O (obtainable by dissolving 0.2 g of FeCl$_2$.4H$_2$O in 20 ml of water) was injected in the flask with an injection cylinder. 0.4 g of NH$_4$OH was added to the mixture in the flask during polymerizing in order to attain adequate oxidizing power. Polymerization was continued for 20 hours from the initiation of polymerization.

Prepared particles were purified by repeating the operations of centrifugal separation/re-dispersion four times using distilled water. In this time, the centrifugal separation was conducted at 20° C. and at rotational speed of 13500 rpm. After the centrifuge separation, supernatant liquid was taken off by decantation, and distilled water was added, and the particles were re-dispersed with a glass rod to obtain magnetic substance-encapsulated particles.

EXAMPLE 14

Magnetic substance-encapsulated particles were prepared by following the same procedure as in Example 13 except for changing an amount of styrene to 2.0 g and an amount of glycidyl methacrylate to 4.0 g.

EXAMPLE 15

Magnetic substance-encapsulated particles were prepared by following the same procedure as in Example 13 except for changing an amount of styrene to 4.0 g and an amount of glycidyl methacrylate to 1.0 g.

EXAMPLE 16

1.0 g of the magnetic substance-encapsulated particle prepared in Example 13 was added to 50 ml of 10% ammonia water and the mixture was stirred at 70° C. for 20 hours. Next, centrifugal washing of the particles was conducted three times using ion-exchanged water and the particles were dispersed in 50 ml of ion-exchanged water. Subsequently, 30 g of ethylene glycol diglycidyl ether was added to this dispersion liquid and mixed, and the mixture was adjusted to pH 11 using a water solution of sodium hydroxide, and then stirred at room temperature for 24 hours. After a reaction, centrifugal washing of a reactant was conducted three times using ion-exchanged water to obtain magnetic substance-encapsulated particles to each of which a linker having an epoxy group was bound.

EXAMPLES 17 AND 18

The respective monomers shown in Table 4 and 800 g of water were put into a two thousands milliliter, four-necked flask. A stirring seal/a stirring rod, a reflux cooling tube and CERAM rubber were attached to the respective necks. This system was put in a thermostatic chamber of 70° C. and the inside of the system was replaced with nitrogen gas for 30 minutes while stirring the contents of the flask at a rotational speed of 200 rpm. Then, 0.2 g of ammonium persulfate which is a polymerization initiator dissolved in water was dissolved in 10 g of water and the resulting solution was injected in the system with an injection cylinder. This time of injection was assumed to be the initiation time of polymerization, and a water solution of $NH_4OH$ (obtainable by dissolving 0.5 g of $NH_4OH$ in 10 g of water) was added to the mixture in the flask during polymerizing in order to attain adequate oxidizing power. And, after a lapse of two minutes from the initiation of polymerization, a water solution of $FeSO_4 \cdot 7H_2O$ (obtainable by dissolving 1.3 g of $FeSO_4 \cdot 7H_2O$ in 20 g of water) was injected in the flask with an injection cylinder. Polymerization was continued for 20 hours from the initiation of polymerization.

Prepared particles were purified by repeating the operations of centrifugal separation/re-dispersion four times using distilled water. In this time, the centrifugal separation was conducted at 20° C. and at rotational speed of 13500 rpm. After the centrifugal separation, supernatant liquid was taken off by decantation, and distilled water was added, and the particles were re-dispersed with a glass rod to obtain magnetic substance-encapsulated particles.

TABLE 4

| Example | GMA | EGDM | St | MMA | HS-10 |
|---|---|---|---|---|---|
| 17 | 25.6 | 1.2 | 2.0 | — | 0.8 |
| 18 | 22.7 | 1.2 | 2.0 | 2.0 | 0.8 |

(unit: g)

An explanation of abbreviations in Table 4 is as follows.
GMA: glycidyl methacrylate
EGDM: ethylene glycol dimethacrylate
St: styrene
MMA: methyl methacrylate
HS-10:

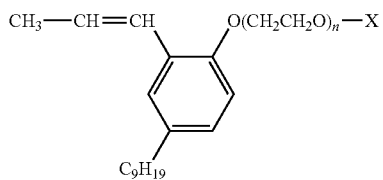

in the formula, X represents $SO_3^-NH_4^+$, and n represents 10.

EXAMPLE 19

1.0 g of the magnetic substance-encapsulated particle prepared in Example 17 was added to 50 ml of 10% ammonia water and the mixture was stirred at 70° C. for 20 hours. Next, centrifugal washing of the particles was conducted three times using ion-exchanged water and the particles were dispersed in 50 ml of ion-exchanged water. Subsequently, 30 g of ethylene glycol diglycidyl ether was added to this dispersion liquid and mixed, and the mixture was adjusted to pH 11 using a water solution of sodium hydroxide, and then stirred at room temperature for 24 hours. After a reaction, centrifugal washing of a reactant was conducted three times using ion-exchanged water to obtain magnetic substance-encapsulated particles to each of which a linker having an epoxy group was bound.

EXAMPLE 20

Particles for immunoassay were prepared from the magnetic substance-encapsulated particles obtained in Example 2.

6 ml of a phosphate buffer (100 mmol/l, pH 7.5) was added to 30 mg of the magnetic substance-encapsulated particle obtained in Example 2, and centrifugal separation was conducted for 20 minutes at a rotational speed of 15000 rpm. To the obtained sediments was added 1 ml of a solution obtainable by dissolving an anti-HBsAg monoclonal antibody in a phosphate buffer (100 mmol/l, pH 7.5) in such a way that the concentration thereof is 0.25 mg/ml, and the mixture was stirred at room temperature for 20 hours and immixed. Then, in order to remove an unreacted anti-HBsAg monoclonal antibody, centrifuge separation was conducted for 20 minutes at a rotational speed of 15000 rpm, and further the obtained sediments were suspended in 6 ml of a phosphate buffer (100 mmol/l, pH 7.5), and centrifuge separation was again conducted for 20 minutes at a rotational speed of 15000 rpm. Then, the obtained sediments was suspended in 6 ml of a solution obtainable by dissolving bovine serum albumin in a phosphate buffer (100 mmol/l, pH 7.5) so as to have the concentration of 1% by weight, and this suspension was stirred at room temperature for 1 hour and blocked to obtain particles for immunoassay, in which the anti-HBsAg monoclonal antibody was bound to the magnetic substance-encapsulated particle.

Next, in order to store the resulting particles for immunoassay at low temperatures, centrifugal separation was conducted for 20 minutes at a rotational speed of 15000 rpm, and the obtained sediments were suspended in 6 ml of a solution obtainable by dissolving bovine serum albumin in a phosphate buffer (100 mmol/l, pH 7.5) so as to have the concentration of 1% by weight and further dissolving sodium azide in the same so as to have the concentration of 0.01% by weight, and this suspension was immediately stored at low temperatures.

EXAMPLES 21, 22 AND 23

Particles for immunoassay were prepared from the magnetic substance-encapsulated particles to each of which a linker was bound, obtained in Example 12, 16 and 19.

1 ml of a 0.1 M borate buffer was added to 12 mg of the magnetic substance-encapsulated particles to each of which a linker was bound, prepared in Example 12, 16 and 19, and centrifugal separation was conducted for 10 minutes at a rotational speed of 15000 rpm to remove a supernatant liquid. To the obtained sediments, 380 µl of a 0.1 M borate buffer and 20 µl of an anti-α-hCG monoclonal antibody solution (5.0 mg/ml) were added, and the mixture was adequately immixed and stirred at room temperature for 20 hours. The centrifugal separation of a reaction solution was conducted for 10 minutes at 15000 rpm to remove an unreacted anti-α-hCG monoclonal antibody. In addition, it was found from measurement of the concentration of protein in the supernatant liquid that an amount of anti-α-hCG monoclonal antibody bound to the magnetic substance-encapsulated particle was 55% of an added amount. The obtained sediments were suspended in 1 ml of a 100 mM phosphate buffer (pH 7.5), and centrifugal separation was again conducted. The sediments was suspended in 900 µl of a solution obtainable by dissolving bovine serum albumin in a 100 mM phosphate buffer (pH 7.5) so as to have the concentration of 5% (w/v), and this suspension was stirred at 37° C. for 1 hour and blocked. Then, centrifugal separation was conducted for 20 minutes at 15000 rpm, and to the sediments, 1 ml of a 0.1 M borate buffer was added, and the mixture was dispersed with ultrasonic vibration. Subsequently, the dispersed sediments was suspended in 1 ml of a solution obtainable by dissolving bovine serum albumin and glycerol in a 100 mM phosphate buffer (pH 7.5), respectively, so as to have the concentration of 5% (w/v), and further dissolving sodium azide in the same so as to have the concentration of 0.01% (w/v) to obtain particles for immunoassay.

COMPARATIVE EXAMPLES 1 TO 3

As Comparative Examples, there were used 3 lots of Estapor M1-030/40 (produced by Merck & Co., Inc.)

COMPARATIVE EXAMPLE 4

Particles for immunoassay were prepared from the magnetic substance-encapsulated particles of Comparative Example 1.

1 ml of a water solution of potassium hydroxide, having a pH of 9.5, was added to 12.5 mg of the magnetic substance-encapsulated particles of Comparative Example 1, and after centrifugal separation was conducted for 10 minutes at 15000 rpm, a supernatant liquid was removed and a surfactant added to the dispersion liquid was removed. Subsequently, to the obtained sediments, 625 µl of a 0.02 M phosphate buffer and 0.625 ml of a 2% carbodiimide solution (PBS buffer) previously prepared were added, and the mixture was stirred for 1.5 hours in a thermostatic chamber of 37° C. The centrifugal separation of a reaction solution was conducted for 10 minutes at 15000 rpm to remove a supernatant liquid, and then to this, 1.2 ml of a 0.02 M phosphate buffer was added, and the mixture was re-dispersed with ultrasonic vibration. By repeating the operation of centrifugal washing described three times, an unreacted carbodiimide was removed. Subsequently, to the obtained sediments, 1.2 ml of a 0.1 M borate buffer was added and 200 µg of an anti-α-hCG monoclonal antibody was added, and the mixture was stirred for a night in a thermostatic chamber of 37° C. On the following day, 50 µl of a 30 mM glycine solution (borate buffer) was added to a reaction solution, and the mixture was stirred for 30 minutes in a thermostatic chamber of 37° C. Then, centrifugal separation was conducted for 10 minutes at 15000 rpm to remove an unreacted anti-α-hCG monoclonal antibody. In addition, it was found from measurement of the concentration of protein in the supernatant liquid that an amount of anti-α-hCG monoclonal antibody bound to the magnetic substance-encapsulated particle was 63% of an added amount. The obtained sediments were suspended in 1 ml of a 100 mM phosphate buffer (pH 6.5), and centrifugal separation was again conducted. The obtained sediments was suspended in 1 ml of a 100 mM phosphate buffer (pH 6.5) adjusted in such a way that the concentration of bovine serum albumin was 1% (w/v), and this suspension was stirred for 30 minutes in a thermostatic chamber of 37° C. and blocked. Then, centrifugal separation was conducted for 10 minutes at 15000 rpm, the sediments was dispersed in 1 ml of a 100 mM phosphate buffer (pH 7.5) adjusted in such a way that concentrations of bovine serum albumin and glycerol were 5% (w/v), respectively, and the concentration of sodium azide was 0.01% (w/v) to obtain particles for immunoassay.

<Evaluation>

(1) Evaluation of Dispersion Stability

Using the magnetic substance-encapsulated particles obtained in Examples 13 to 18 and the magnetic substance-encapsulated particles obtained in Comparative Examples 1 to 3, a dispersion liquid having a solid matter content of 1% was prepared and after dispersion through ultrasonic vibration, it was left standing, and the occurrence of precipitated particles was visually observed. In the case of using the magnetic substance-encapsulated particles of Comparative Examples 1 to 3, the precipitation of the particles was partially recognized soon after the dispersion of the particles. Further, a precipitated layer was formed at the bottom of a sample bottle on the day following the still standing and therefore it was found that these particles have low dispersion stability. On the other hand, in the magnetic substance-encapsulated particles of Examples 13 to 18, no precipitated substance was found on the day following the still standing and therefore it was found that these particles have high dispersion stability.

(2) Evaluation of Shape of Particle

The magnetic substance-encapsulated particles obtained in Examples 13 to 18 and the magnetic substance-encapsulated particles obtained in Comparative Examples 1 to 3 were diluted with water and deposited and fixed on a collodion membrane supported by a metal mesh, and the shape of the particles deposited were observed with a transmission electron microscope (TEM).

Average particle sizes of the magnetic substance-encapsulated particles and the magnetic substances, observed with the TEM, are shown in Table 5.

TABLE 5

| | Average particle size (nm) | |
|---|---|---|
| | magnetic substance-encapsulated particle | magnetic substance |
| Example 13 | 230 | 5 |
| Example 14 | 190 | 6 |
| Example 15 | 320 | 4 |
| Example 16 | 230 | 5 |
| Example 17 | 115 | 6 |
| Example 18 | 100 | 8 |
| Comparative Example 1 | 370 | 20 |
| Comparative Example 2 | 410 | 21 |
| Comparative Example 3 | 520 | 24 |

From Table 5, it was observed all of the magnetic substance-encapsulated particles obtained in Examples 13, 14, 15 and 16 are spherical particles having a uniform particle size and contain the magnetic substance within a particle. On the other hand, in any of Comparative Examples 1 to 3, the magnetic substance-encapsulated particles having particle sizes of 100 to 1000 μm are present and a particle size is nonuniform. Further, in any of Comparative Examples 1 to 3, it was recognized that the magnetic substances were exposed at the surfaces of the magnetic substance-encapsulated particles.

Further, in order to verify that the magnetic substance-encapsulated particles prepared in Examples 13, 14, 15 and 16 are attracted to a magnet, a small amount of a dispersion liquid of the magnetic substance-encapsulated particle was put in a 1.5 ml microtube and appropriately diluted with distilled water, and the microtube was stood up on a microtube-stand (manufactured by DYNAL BIOTECH, MPC (registered trademark)-M) and it was visually confirmed that the dispersed magnetic substance-encapsulated particles were attracted to a magnet.

(3) Evaluation of Variations in Content of Magnetic Substance

Using a particle analyzer (DP-1000, manufactured by HORIBA, Ltd.), each deviation of measurement data was determined by measuring synchronous luminescence of a carbon element composing an organic polymer material and a metal element composing a magnetic substance on magnetic substance-encapsulated particles of Examples 15 to 18 and Comparative Examples 1 to 3. The results are shown in Table 6.

TABLE 6

| Sample | | Deviation |
|---|---|---|
| Example | 15 | 0.1160 |
| | 16 | 0.1198 |
| | 17 | 0.2504 |
| | 18 | 0.2417 |
| Comparative Example | 1 | 0.3451 |
| | 2 | 0.2843 |
| | 3 | 0.3988 |

Performing a comparison between the deviations of the magnetic substance-encapsulated particles of Examples and Comparative Examples, it is found that the deviations of the magnetic substance-encapsulated particles of Examples 15 to 18 are small and the variations in the magnetic substance content are small. On the other hand, it becomes evident that the magnetic substance-encapsulated particles of Comparative Examples 1 to 3 have a large deviation and large variations in the magnetic substance content.

(4) Evaluation 1 of Chromatogram Developing Property (4)-1 Verification of Chromatogram Developing Property The particles for immunoassay in Examples 21, 22 and Comparative Example 4 were dispersed in a physiological saline, adjusted in such a way that the concentration of bovine serum albumin was 1% (w/v) and the concentration of triton-100 was 0.03% (w/v), so as to have the solid content of 0.045% (w/v). 30 μl of the dispersion liquid of each case was spotted on a nitrocellulose membrane (SRHF P70 produced by Millipore Corporation) having a pore size of 10 to 12 μm and the dispersion liquid was developed in circle form. Each of the developed dispersion liquid was in the form of a circle having a diameter of about 18 mm. Then, each dispersion liquid was dried, and a diameter of a circle colored by the development of the magnetic substance-encapsulated particle was measured. Consequently, the diameter in the case of using the particles for immunoassay in Examples 18 was 16 mm, the diameter in the case of using the particles for immunoassay in Examples 19 was 17 mm and the diameter in the case of using the particles for immunoassay in Comparative Examples 4 was 12 mm.

In Examples 21, 22, it was found that the particles for immunoassay are developed smoothly with a developing medium in a chromatogram carrier since a developing region of particles for immunoassay reaches 92% of a developing region of a medium. On the other hand, in Comparative Example 4, since the developing region is about 70% of a developing region of a medium, particles for immunoassay of Comparative Example 4 is low in a developing property compared with those of Example 21 or 22. And, it was found that in Comparative Example 4, coloring around the center of a spot was dense and developing was nonuniform.

(4)-2 Preparation of Specimen

A nitrocellulose membrane (SRHF P70, produced by Millipore Corporation) was cut in a size of 20 cm width×6 cm length, and to a portion (reaction portion) which is at a distance of 3 cm from a top end of the direction of the length, a solution obtainable by dissolving an anti-β-hCG monoclonal antibody in a tris-hydrochloric acid buffer (10 mmol/l, pH 7.4) so as to have the concentration of 2.0 mg/ml was applied in the form of a straight-line with a width of 0.7 mm. Then, this applied membrane was dried at 37° C. for 2 hours, and then immersed for 1 hour in a solution obtainable by dissolving bovine serum albumin (produced by Wako Pure Chemical Industries, Ltd.) in a phosphate buffer (100 mmol/l, pH 7.5) so as to have the concentration of 1% by weight, and blocked. And then, this blocked membrane was washed with a solution obtainable by dissolving sodium laurylbenzene sulfonate in a phosphate buffer (100 mmol/l, pH 7.5) so as to have the concentration of 0.1% by weight, and then dried at room temperature in a silica gel desiccator to obtain a specimen to which the anti-β-hCG monoclonal antibody was fixed.

The obtained specimen was cut in a size of 5 mm in width, and a water absorbing pad having a size of 5 mm width×20 mm length (AP22, produced by Millipore Corporation) was overlaid at a top end of the direction of the length and a conjugated pad having a size of 5 mm width×15 mm length (glass fiber, produced by Millipore Corporation) was overlaid at a bottom end of the direction of the length, and they were fixed with a transparent tape to prepare a specimen.

(4)-3 Implementation of Immunoassay

Each of the particles for immunoassay of Examples 21 to 23 and Comparative Example 4 were dispersed in physiological salines of testing liquids, respectively, adjusted in such a way that the concentration of bovine serum albumin was 1% (w/v) and the concentration of triton-100 was 0.03% (w/v), and the concentration of hCG was 0 mIU/ml, 25 mIU/ml, 100 mIU/ml, 1000 mIU/ml and 5000 mIU/ml, so as to have the concentration of 0.05% (w/v).

Next, to the prepared conjugated pad of a specimen, 100 µl of the testing liquid in which hCG had a specified concentration was added dropwise.

After a lapse of 10 minute from adding dropwise, in the case of using the particles for immunoassay of Examples 21 to 23, coloring due to the particles for immunoassay was found at a reaction portion in specimens other than specimen in which the concentration of hCG was 0 mIU/ml. And, it was confirmed that a degree of this coloring depends on the concentration of hCG. And, the magnetism corresponding to the concentration of the hCG was recognized at a reaction point and these particles for immunoassay were shown to be effective for the method of immunoassay using the magnetism as a marker.

On the other hand, in the case of using the particles for immunoassay of Comparative Example 4, coloring due to the particles for immunoassay was found at a reaction portion and at portions up to a reaction portion in every specimen. Particularly, it was found that the coloring around the portion where the conjugated pads were overlaid was strong and the particles for immunoassay were retained, and that in the case of hCG of 1000 mIU/ml or more, its portion was more densely colored than the reaction portion. In the case of using the particles for immunoassay of Comparative Example 4, these particles for immunoassay were shown to be not adaptable to the method of immunoassay using the magnetism as a marker, because (1) the particles for immunoassay were retained at a specimen, (2) an amount of the particles for immunoassay developing varied with the concentrations of a material to be detected, and (3) even when a material to be detected did not exist (hCG: 0 mIU/ml), the particles for immunoassay were captured at a reaction portion in a non-specific manner.

(5) Evaluation 2 of Chromatogram Developing Property (5)-1 Preparation of Specimen A nitrocellulose membrane (SRHF, produced by Millipore Corporation) was cut in a size of 30 cm width×6 cm length, and to a portion (reaction portion) which is at a distance of 3 cm from a top end of the direction of the length, a solution obtainable by dissolving anti-HBs Ag monoclonal antibody having a reaction epitope different from that used in the particles for immunoassay of Example 20 in a tris-hydrochloric acid buffer (10 mmol/l, pH 7.4) so as to have the concentration of 2.0 mg/ml was applied in the form of a straight-line with a width of 0.7 mm. Then, this applied membrane was dried at 37° C. for 2 hours, and then immersed for 1 hour in a solution obtainable by dissolving bovine serum albumin (produced by Wako Pure Chemical Industries, Ltd.) in a phosphate buffer (100 mmol/l, pH 7.5) so as to have the concentration of 1% by weight, and blocked. And then, this blocked membrane was washed with a solution obtainable by dissolving sodium laurylbenzene sulfonate in a phosphate buffer (100 mmol/l, pH 7.5) so as to have the concentration of 0.1% by weight, and then dried at room temperature in a silica gel desiccator to obtain a membrane to which the anti-HBsAg monoclonal antibody was fixed.

The obtained membrane to which the anti-HBsAg monoclonal antibody was fixed was cut in a size of 5 mm in width, and a filter paper for absorbing water having a size of 5 mm width×2 cm length (produced by Millipore Corporation) was overlaid at a top end of the direction of the length and fixed with a transparent tape to prepare a specimen.

(5)-2 Implementation of Immunoassay

A solution, obtainable by dissolving the particles for immunoassay of Example 20 in a phosphate buffer (100 mmol/l, pH 7.5) so as to have the concentration of 0.1% by weight, further by dissolving bovine serum albumin in the same so as to have the concentration of 1% by weight and further dissolving sodium azide in the same so as to have the concentration of 0.01% by weight, was prepared, and 20 µl of this solution was put in each well of 96 well micro plate (manufactured by Nalge Nunc International K.K.).

Next, standard articles of a HBs antigen (50 IU/ml) were diluted with a phosphate buffer (100 mmol/l, pH 7.5) so as to have a specified concentration, and 100 µl of each standard article was put in a well and mixed, and then the specimen was put in a well and the well was erected.

The specimen was taken out after a lapse of 30 minutes. Consequently, the magnetism corresponding to the concentration of the HBs antigen was recognized at a reaction point and the particles for immunoassay of Example 20 was shown to be effective for the method of immunoassay using the magnetism as a marker.

INDUSTRIAL APPLICABILITY

In accordance with the present invention, it is possible to obtain the magnetic substance-encapsulated particles which have uniform magnetism and a narrow particle size distribution by simultaneously performing a reaction of copolymerizing a monomer not having a hydrophilic group and a monomer having a hydrophilic group to form a particle and a reaction of modifying a metal ion while taking in the metal ion into a particle to form a magnetic substance. By adsorbing and binding an antigen or an antibody to the magnetic substance-encapsulated particle of the present invention, particles for immunoassay of the present invention can be obtained. And, a sensitive and precise measurement becomes possible by performing a method of immunoassay using the magnetic substance-encapsulated particles or the particles for immunoassay of the present invention. Further, a sensitive and precise measurement becomes possible by performing a method of immunoassay using the magnetic substance-encapsulated particles of the present invention as a marker.

And, when a linker is introduced into the magnetic substance-encapsulated particle of the present invention, it becomes possible to enhance the reactivity of, for example, an antigen, an antibody or an agent to bind to the magnetic substance-encapsulated particle, that is, a sensitive and precise measurement becomes possible, and even when the particle surface of the magnetic substance-encapsulated particle of the present invention is non-adsorbent against protein, it becomes possible to bind the antigen or the antibody to the magnetic substance-encapsulated particle with reliability because the linker has a binding property to protein.

The invention claimed is:

1. A magnetic substance-encapsulated particle, which comprises an organic polymer material and a magnetic substance, wherein the magnetic substance has an average particle size of 1 to 30 nm, the magnetic substance being dispersed and encapsulated within the organic polymer material of said particle; wherein said organic polymer material comprises a monomer not having a hydrophilic group for forming a core of said particle and a monomer having a hydrophilic group for forming a shell of said particle and forming a particle having dispersion stability in water; and wherein an absolute deviation of a component ratio between a carbon element comprising the organic polymer material and a metal element comprising the magnetic substance is 0.27 or less, wherein the monomer not having a hydrophilic group comprises a monomer having a glycidyl group and a styrenic monomer and wherein the monomer having a hydrophilic group is polyethylene glycol (meth)acrylate represented by the following general formula (1) or a compound represented by the following general formula (2):

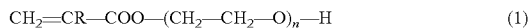

in the formula, R represents H or $CH_3$, and n represents an integer of 1 to 20,

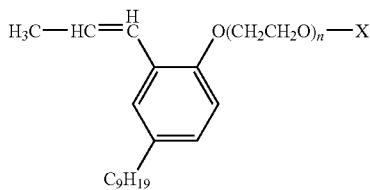

in the formula, X represents H or $SO_3^- NH_4^+$, and n represents an integer of 3 to 30.

2. The magnetic substance-encapsulated particle according to claim 1,
wherein the magnetic substance is formed by oxidization of a metal ion within a particle in a polymerization process of forming the magnetic substance-encapsulated particle.

3. The magnetic substance-encapsulated particle according to claim 2, wherein the metal ion is an iron ion.

4. The magnetic substance-encapsulated particle according to claim 1,
wherein the proportion of a monomer unit derived from the styrenic monomer in the organic polymer material is 5 to 90% by weight.

5. The magnetic substance-encapsulated particle according to claim 1, wherein the organic polymer material is crosslinked.

6. The magnetic substance-encapsulated particle according to claim 1, which has at least a functional group selected from the group consisting of a carboxyl group, a hydroxyl group, an epoxy group, an amino group, a triethylammonium group, a dimethylamino group and a sulfonic acid group at the surface of the particle.

7. The magnetic substance-encapsulated particle according to claim 1, wherein an average particle size is 0.05 to 1 μm.

8. The magnetic substance-encapsulated particle according to claim 1, wherein a content of the magnetic substance is 0.1 to 50% by weight.

9. The magnetic substance-encapsulated particle according to claim 1, wherein an average particle size of the magnetic substance is 2 to 10 nm.

10. The magnetic substance-encapsulated particle according to claim 1, wherein a linker having a functional group capable of forming a covalent bond with an antigen or an antibody binds to a particle surface.

11. The magnetic substance-encapsulated particle according to claim 10,
wherein the functional group capable of forming a covalent bond with an antigen or an antibody is an epoxy group.

12. The magnetic substance-encapsulated particle according to claim 10, wherein the linker is polyethylene glycol diglycidyl ether.

* * * * *